US011259714B2

(12) United States Patent
Gruionu et al.

(10) Patent No.: US 11,259,714 B2
(45) Date of Patent: Mar. 1, 2022

(54) SYSTEM AND METHOD FOR MEASURING SOLID STRESS IN TISSUES (71) Applicants: Gabriel Gruionu, Somerville, MA (US); Lucian Gruionu, Craiova (RO); Lance L. Munn, Lexington, MA (US); Rakesh K. Jain, Wellesley, MA (US)

(72) Inventors: Gabriel Gruionu, Somerville, MA (US); Lucian Gruionu, Craiova (RO); Lance L. Munn, Lexington, MA (US); Rakesh K. Jain, Wellesley, MA (US)

(73) Assignee: The General Hospital Corporation, Boston, MA (US)

(*) Notice: Subject to any disclaimer, the term of this patent is extended or adjusted under 35 U.S.C. 154(b) by 365 days.

(21) Appl. No.: 14/892,380

(22) PCT Filed: May 21, 2014

(86) PCT No.: PCT/US2014/038937
§ 371 (c)(1),
(2) Date: Nov. 19, 2015

(87) PCT Pub. No.: WO2014/190034
PCT Pub. Date: Nov. 27, 2014

(65) Prior Publication Data
US 2016/0089043 A1 Mar. 31, 2016

Related U.S. Application Data (60) Provisional application No. 61/826,781, filed on May 23, 2013, provisional application No. 61/862,475, filed on Aug. 5, 2013.

(51) Int. Cl.
A61B 5/03 (2006.01)
A61B 1/00 (2006.01)
(Continued)

(52) U.S. Cl.
CPC ............ *A61B 5/03* (2013.01); *A61B 1/0008* (2013.01); *A61B 5/0093* (2013.01);
(Continued)

(58) Field of Classification Search
CPC ........ A61B 5/03; A61B 1/0008; A61B 5/0093
(Continued)

(56) References Cited

U.S. PATENT DOCUMENTS 3,474,776 A   10/1969 O'Brien
3,724,274 A * 4/1973 Millar .................. A61B 5/0215
                                                       73/726

(Continued)

OTHER PUBLICATIONS

International Search Report and Written Opinion dated Oct. 23, 2014 in connection with PCT/US2014/38937.

*Primary Examiner* — Daniel L Cerioni
(74) *Attorney, Agent, or Firm* — Quarles & Brady LLP (57) ABSTRACT A system and method is configured for use with an endoscope, a biopsy needle, and a data acquisition system. The system includes a sensor tip and a pressure sensor coupled to the sensor tip and having at least one piezo-resistor component with an internal-facing side and an external-facing side, and an opening adjacent to the at least one piezo-resistor component to allow fluid access to the internal-facing side and the external-facing side. The system also includes a tubing member with a distal end and a proximal end, the sensor tip coupled to the distal end, the sensor tip and the tubing member configured to be routed through the biopsy needle and connection elements coupled to the proximal end of the tubing member, the connection elements configured to mount the tubing member relative to the biopsy needle and to couple the pressure sensor to the data acquisition system.

12 Claims, 9 Drawing Sheets (51) Int. Cl.
*A61B 10/02* (2006.01)
*A61B 5/00* (2006.01)
*A61B 8/00* (2006.01)
*A61B 8/12* (2006.01)
*A61B 8/08* (2006.01)
*A61B 10/04* (2006.01)

(52) U.S. Cl.
CPC ........ *A61B 10/0233* (2013.01); *A61B 8/0841* (2013.01); *A61B 8/12* (2013.01); *A61B 8/4494* (2013.01); *A61B 2010/045* (2013.01); *A61B 2562/0247* (2013.01)

(58) Field of Classification Search
USPC ........................................................ 600/561
See application file for complete search history.

(56) References Cited

U.S. PATENT DOCUMENTS

| | | | |
|---|---|---|---|
| 3,905,356 A | | 9/1975 | Fletcher et al. |
| 5,396,897 A | | 3/1995 | Jain et al. |
| 6,078,830 A | * | 6/2000 | Levin .................. A61B 18/1492 |
| | | | 600/374 |
| 6,112,598 A | * | 9/2000 | Tenerz .................. A61B 5/0215 |
| | | | 73/756 |
| 6,264,612 B1 | | 7/2001 | McConnell et al. |
| 6,546,787 B1 | | 4/2003 | Schiller et al. |
| 6,790,186 B1 | | 9/2004 | Field et al. |
| 2005/0256387 A1 | | 11/2005 | Omata |
| 2006/0051734 A1 | | 3/2006 | McNeill et al. |
| 2006/0189891 A1 | | 8/2006 | Waxman et al. |
| 2008/0300571 A1 | * | 12/2008 | LePivert ............. A61B 18/1492 |
| | | | 604/503 |

\* cited by examiner

SYSTEM AND METHOD FOR MEASURING SOLID STRESS IN TISSUES

CROSS-REFERENCE TO RELATED APPLICATIONS

This application represents the national stage entry of PCT International Application No. PCT/US2014/038937 filed May 21, 2014, which claims priority to and incorporates herein by reference U.S. Provisional Patent Applications Ser. No. 61/826,781, filed May 23, 2013, and Ser. No. 61/862,475, filed Aug. 5, 2013, the contents of which are hereby incorporated by reference in their entirety for all purposes.

BACKGROUND

The present disclosure is directed to a system and method for measuring the solid stress in soft tissues and, more particularly, a system and method for measuring the solid stress in tumors for, for example, monitoring tumor progression and/or response to treatment.

Tumor biopsies are routinely collected, for example, via a catheter-based biopsy needle or forceps, at different periods during treatment for diagnosis and staging of disease. In addition, tumor interstitial pressure could be measured as a biomarker for monitoring tumor progression and response to treatment. For example, interstitial fluid pressure is measured using an open lumen needle inserted into the tumor. The pressure generated by a column of fluid inside the needle is proportional to the interstitial fluid pressure in the tumor.

In addition to fluid-phase pressures, such as interstitial fluid pressure, the mechanical environment of a tumor is also characterized by solid-phase pressures, such as solid or residual stress. Recently, it has been demonstrated that tumor residual stress (that is, stress contained in structural, visco-elastic elements of the tumor such as cell membranes, cytoskeletal elements and matrix components) can be used as a biomarker for tumor response to chemo- and anti-stromal therapies in a variety of tumors. That is, lower residual stress inside a tumor is indicative of less-compressed tumor blood vessels and can result in more effective cancer therapy. However, there are no clinical approaches for obtaining an accurate representation of the stress levels contained in the compressed cells and matrix components (that is, the solid stress) of a tumor.

For example, the present way to evaluate the degree of solid stress in a tumor is by measuring the residual stress, an approximation of the solid stress, by removing the tumor from the body and then cutting the excised tumor with a scalpel blade. As the tumor is cut, the tissue relaxes and the width of the incision increases over time (such as a few minutes). The opening angle of this incision, which can be measured, is proportional to the residual stress present in the tumor. This type of approach, however, is often not feasible in a clinical setting. In addition, the above-described open-lumen needle approach for measuring interstitial pressure corresponds strictly to the fluid pressure and cannot distinguish fluid pressure from solid pressure.

Therefore, it would be desirable to provide a clinically useful, minimally-invasive system and method for measuring solid stress in tumors.

SUMMARY

The present disclosure overcomes the aforementioned drawbacks by providing an in vivo and minimally invasive system and method to measure solid stress in a human soft tissue. More specifically, a catheter-based system is provided to guide a device into tumor tissue. The device is provided with an electro-mechanical microsensor for measuring tissue solid stress separate from interstitial fluid pressure. This is accomplished by enabling equalization of fluid pressure on both external-facing and internal-facing sides of the electro-mechanical microsensor. Due to the use of the catheter-based system, solid stress measurements can be obtained during routine tumor biopsy procedures.

In accordance with one implementation of the disclosure, a device for measuring solid stress in a tissue is provided. The device includes a sensor tip and a tubing member with a distal end and a proximal end, wherein the sensor tip is coupled to the distal end. The device also includes connection elements coupled to the proximal end of the tubing member and an electro-mechanical pressure microsensor coupled to the sensor tip. The electro-mechanical pressure microsensor includes an internal-facing side and an external-facing side, and an opening to allow fluid access to the internal-facing side and the external-facing side.

In accordance with another implementation of the disclosure, a device for measuring solid stress in a tumor and configured for use with a system including an endoscope, a biopsy needle, and a data acquisition system is provided. The device includes a sensor tip and a pressure sensor coupled to the sensor tip. The pressure sensor includes at least one piezo-resistor component with an internal-facing side and an external-facing side, and an opening adjacent to the at least one piezo-resistor component to allow fluid access to the internal-facing side and the external-facing side. The device also includes a tubing member with a distal end and a proximal end, wherein the sensor tip is coupled to the distal end and the sensor tip and the tubing member are configured to be routed through the biopsy needle. The device further includes connection elements coupled to the proximal end of the tubing member and configured to mount the tubing member relative to the biopsy needle and to couple the pressure sensor to the data acquisition system.

In accordance with yet another implementation of the disclosure, a method for measuring solid stress in a tumor is provided. The method includes providing a biopsy needle with a pressure sensor routed through the biopsy needle until the pressure sensor is positioned within a distal tip of the biopsy needle, advancing the distal tip of the biopsy needle to a predefined depth within the tumor to create a cylindrical opening within the tumor, and retracting the distal tip of the biopsy needle so that the pressure sensor is exposed within the cylindrical opening. The method also includes obtaining solid stress measurements of tissue surrounding the cylindrical opening as the tissue relaxes against the pressure sensor and retracting the pressure sensor and the biopsy needle out of the tumor.

These and other features and advantages of the present invention will become apparent upon reading the following detailed description when taken in conjunction with the drawings.

DETAILED DESCRIPTION

The present disclosure provides a minimally-invasive system and method for measuring residual/solid stress in a tumor. As used herein, internal or residual/solid stress is a stress generated by either tumor or stroma cells (for example, everything other than the tumor cells). The system utilizes a biopsy needle catheter introduced in an endoscope. A pressure sensor (such as an electro-mechanical pressure microsensor) introduced in the tumor environment, via the biopsy needle, is used to measure the solid stress separately from the hydrostatic fluid pressure. The biopsy needle catheter allows use of the system with existing endoscopic tools during a standard biopsy collection procedure.

The present disclosure recognizes that tumor solid stress (that is, stress stored within visco-elastic elements of the tumor) can be used as a biomarker for tumor response to chemotherapy. It has been recently shown that malignant tumors express a high level of residual stress, which can be responsible for compression of tumor blood vessels and decreased efficiency of tumor therapy. Therefore, reduction of residual stress can result in a better delivery of chemotherapy agents to the tumor and more efficient treatment of the tumor. This concept may provide superiority over existing tumor therapy monitoring methods. Thus, for example, measurements of tumor solid stress can be used to monitor tumor progression with and without chemotherapy treatment, and can also inform treatment decisions, including whether chemotherapy should be used alone or in combination with other therapy. As will be described, a tumor sensor is provided that is designed to measure the internal or residual/solid stress.

Currently, tumor biopsies are routinely collected via a catheter-based biopsy needle or forceps inserted through the working channels of an endoscope at different stages during treatment to diagnose and stage the disease. The system of the present disclosure incorporates a catheter-based technology, for example, to be used at the same time with the biopsy collection. The system includes a device that incorporates an electro-mechanical pressure microsensor to accurately measure the residual stress at the same site where the biopsy is collected without disrupting the currently established diagnostic and treatment protocols.

Figure 1A:
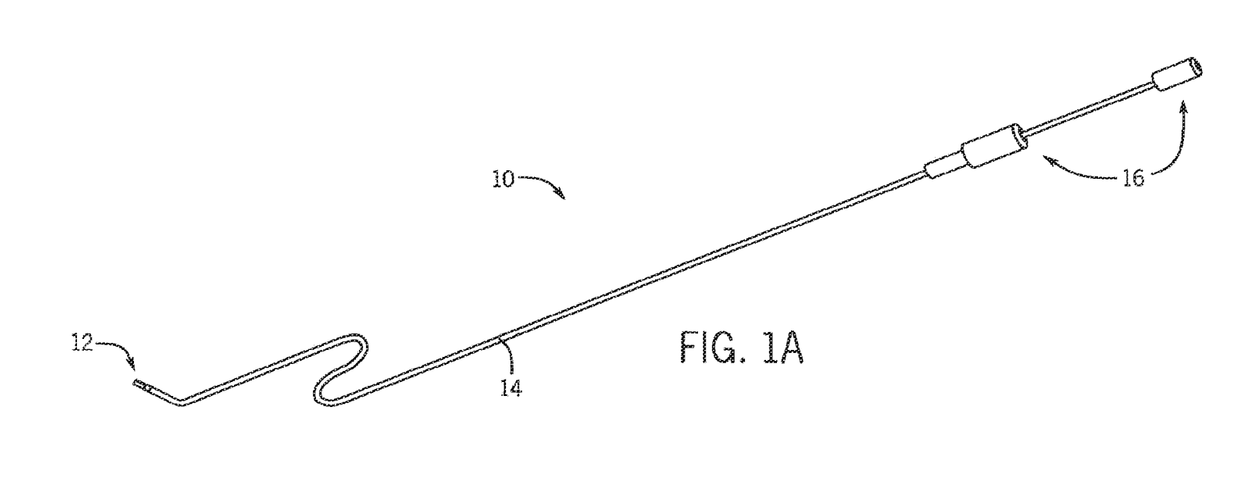
FIG. 1A is perspective view of a device for measuring solid stress in a tissue in accordance with one implementation of the present disclosure.
Figure 1B:
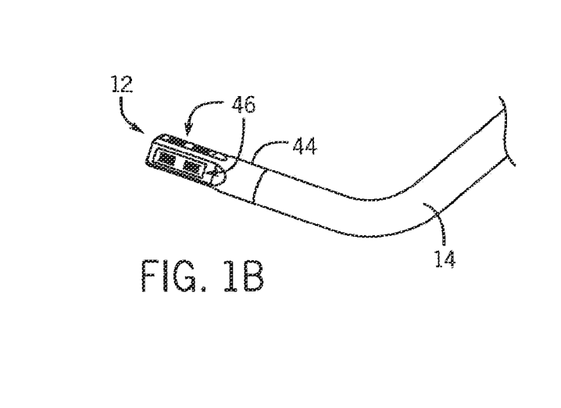
FIG. 1B is a perspective view of a solid stress sensor of the device of FIG. 1A.
Figure 1C:
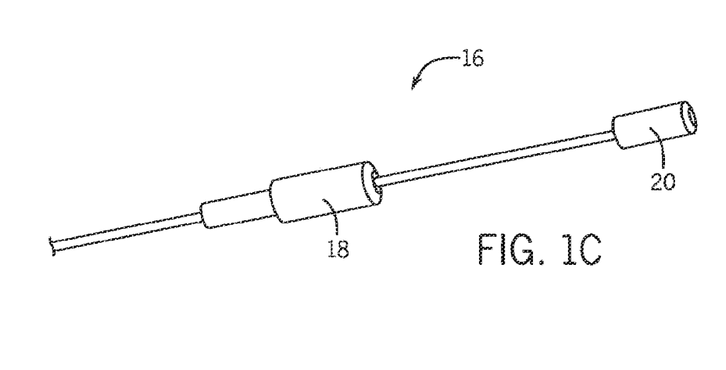
FIG. 1C is a perspective view of connection elements of the device of FIG. 1A.

More specifically, as shown in FIGS. 1A-1C, the device 10 can include a solid stress sensor 12 (a first member), tubing 14 (a second member), and connection elements 16 (a third member). The tubing 14 can be flexible metal tubing that mechanically and electrically connects the solid stress sensor 12 and the connection elements 16. The connection elements 16 can include a biopsy needle mounting element 18 configured to couple the tubing 14 to an external device (such as a biopsy catheter of the system, described below), and a data connector 20 configured to connect the device 10 to a data acquisition system 22 (or personal computer or other data procession system), as shown in FIG. 2, for data collection and processing.

Figure 2:
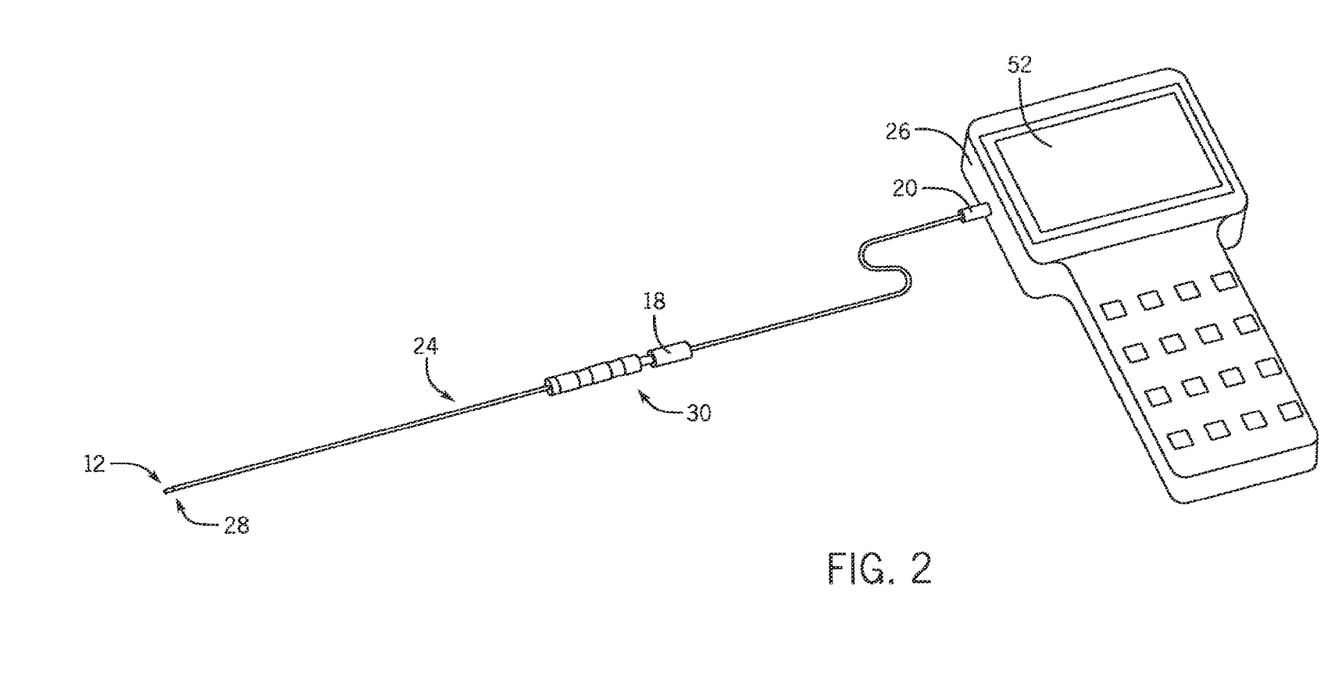
FIG. 2 is a partial perspective view of a system for measuring solid stress in a tissue in accordance with one implementation of the present disclosure.
Figure 3A:
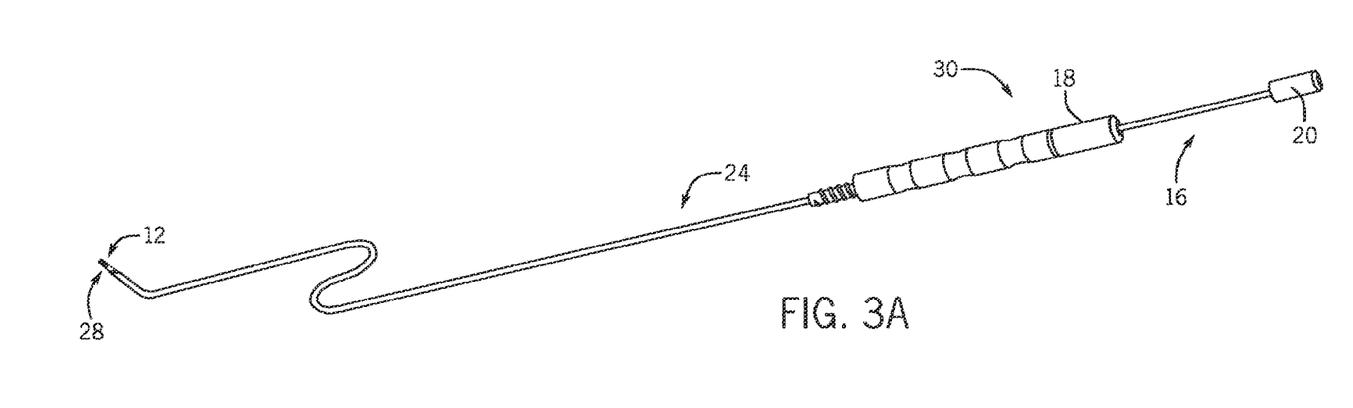
FIG. 3A is a perspective view of the device of FIG. 1A routed through a biopsy needle.
Figure 3B:
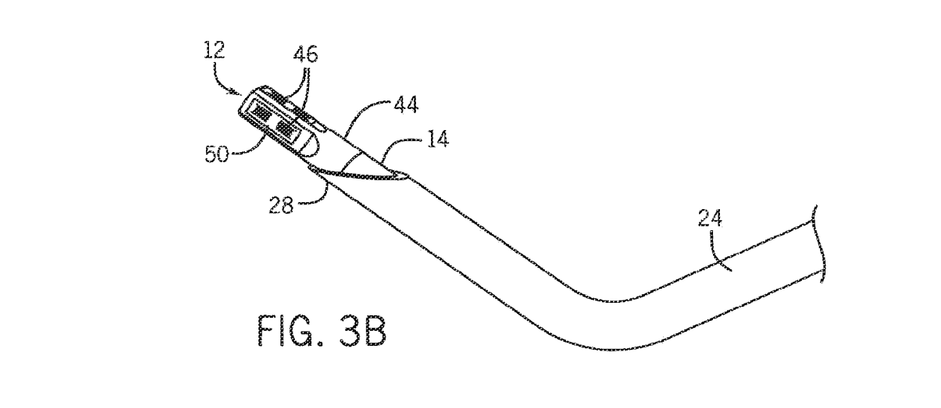
FIG. 3B is a perspective view of the solid stress sensor of the device extending outward from a needle tip of the biopsy needle of FIG. 3A.
Figure 4A:
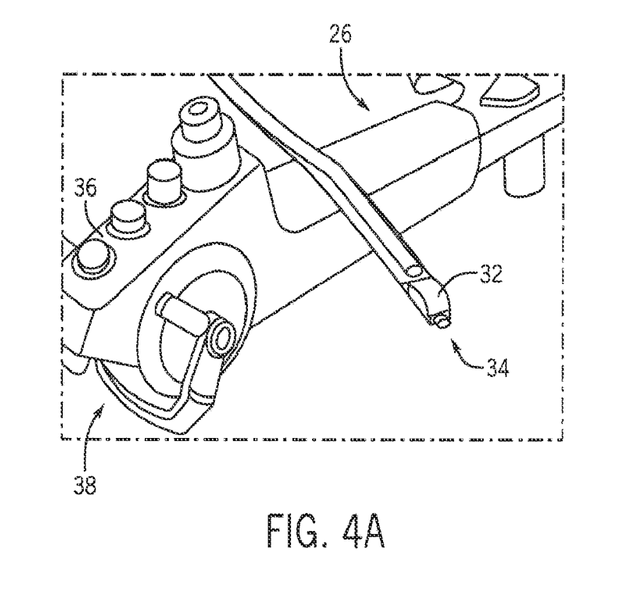
FIG. 4A is a perspective view of an ultrasound-guided endoscope for use with implementations of the present disclosure.
Figure 4B:
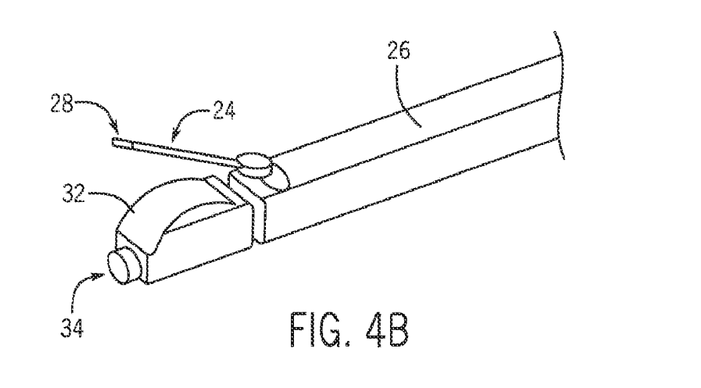
FIG. 4B is a perspective view of a distal end of the ultrasound-guided endoscope of FIG. 4A.

In addition to the device 10, the system can include a biopsy needle 24, as shown in FIGS. 2-3B, and an endoscope 26, such as that shown in FIGS. 4A and 4B. With reference to the biopsy needle 24, as shown in FIGS. 2-3B, the device 10 can be routed through the biopsy needle 24, so that the solid stress sensor 12 is positioned adjacent to a distal end or tip 28 of the biopsy needle 24 and the biopsy needle mounting element 18 can be mounted on or positioned adjacent to a proximal end 30 of the biopsy needle 24. Accordingly, the tubing 14 and the solid stress sensor 12 can be sized to enable such routing through the biopsy needle 24. By moving the biopsy needle 24 relative to the device 10, as further described below, the solid stress sensor 12 can be retracted within the needle tip 28 or extended outward from the needle tip 28, as best shown in FIG. 3B.

Figure 5A:
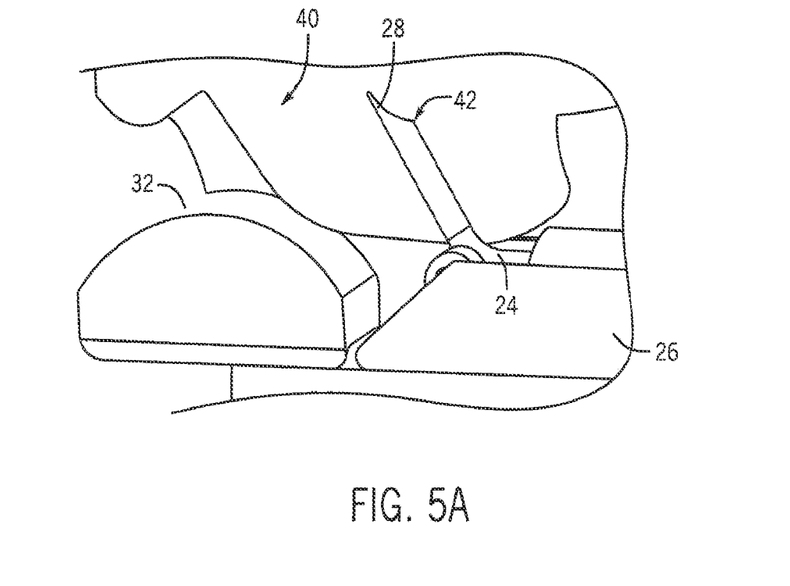
FIGS. 5A and 5B are partial perspective views of the device of FIG. 1A routed to a tumor site in a "penetrating position" and a "sensing position," respectively.
Figure 5B:
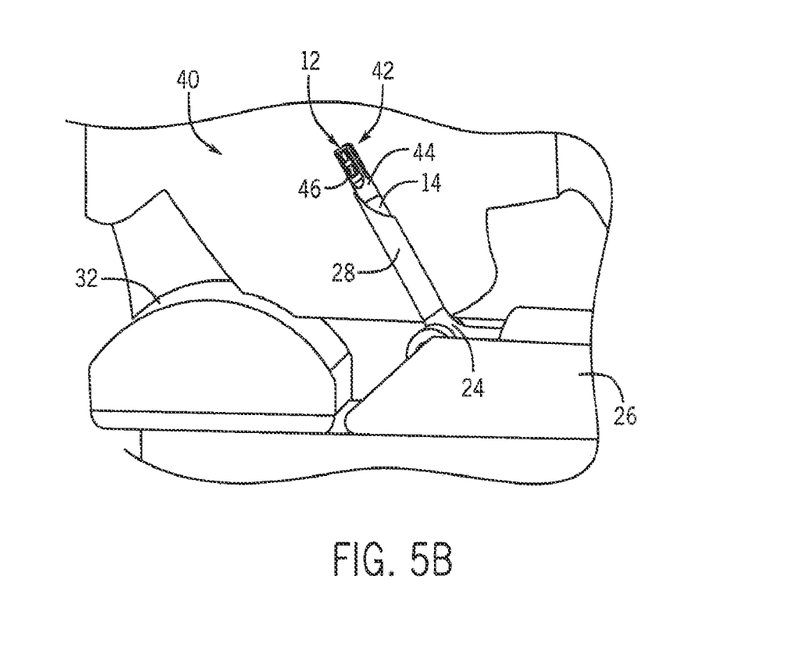

With reference to the endoscope 26, an ultra-sound guided endoscope 26 can be used in some applications, such as that manufactured by Pentax® Medical Company. As shown in FIGS. 4A-5B, the endoscope 26 can include an ultrasound transducer 32 at or near its distal end 34. Furthermore, as shown in FIG. 4A, the endoscope 26 can include a handle portion 36 at its proximal end 38. The biopsy needle 24 and the device 10 can be routed through the endoscope 26 in a conventional manner so that the biopsy needle 24 and the solid stress sensor 12 protrude from the distal end 34 of the endoscope 26, as shown in FIGS. 4B, 5A, and 5B. Through conventional procedures, a user can guide the biopsy needle 24 and the solid stress sensor 12 to a tumor site 40 of a subject via the endoscope 26, as shown in FIGS. 5A and 5B. In addition, the biopsy needle tip 28 can be sharp to facilitate penetrating tissue as it is guided toward the tumor site 40. For example, the biopsy needle tip 28 can be a traditional semi-circular tip or a full circular tip for more even penetration of tissue.

As described above, the solid stress sensor 12 can be positioned within the distal end 28 of the biopsy needle 24 (as shown in FIG. 5A) or the biopsy needle 24 can be retracted to allow the solid stress sensor 12 to be positioned outward past the distal end 28 of the biopsy needle 24 (as shown in FIG. 5B). More specifically, in operation, the device 10 can be delivered to the tumor site 40 through ultrasound guidance (that is, using the ultrasound transducer 32 at the distal end 34 of the endoscope 26) so that the biopsy needle tip 28 is positioned inside the tumor 40. For example, the biopsy needle tip 28 can be advanced into the tumor 40 until it reaches the center of the tumor 40 or another pre-defined depth. The biopsy needle tip 28 piercing the tumor 40 causes a cylindrical opening 42 within the tumor 40, at this time filled by the biopsy needle tip 28. During delivery and advancement of the biopsy needle tip 28 into the tumor 40, the device 10 and, more specifically, the solid stress sensor 12, can remain entirely within the biopsy needle 24, as shown in FIG. 5A. This can be considered a "penetrating position" of the system.

After the biopsy needle tip 28 has pierced the tumor 40, the biopsy needle 24 can be retracted (that is, by a user) so that the solid stress sensor 12 remains within and exposed to the cylindrical opening 42 created by the biopsy needle tip 28, as shown in FIG. 5B. This can be considered a "sensing position" of the system. Once in the sensing position, the solid stress sensor 12 can record solid stress measurements for a time period (such as about thirty seconds to about sixty seconds), as further described below. Following this time period, the solid stress sensor 12 can be retracted back into the biopsy needle 24. The endoscope 26 and biopsy needle 24 can then be moved out of the tumor 40 (and/or out of the subject entirely) or advanced to another position within the tumor 40. In some applications, the advancement of the biopsy needle 24 can be performed from more shallow to deeper positions within the tumor 40 to avoid tissue disruption prior to data collection.

With further reference to the solid stress sensor 12, in some applications, the solid stress sensor 12 can include a sensor tip 44 with one or more electro-mechanical pressure microsensors 46 ("pressure sensors" or "electro-mechanical microsensors"), such as piezo-resistive sensors, positioned around the sensor tip 44. For example, the solid stress sensor 12 can include between one and four pressure sensors 46 positioned around its outer perimeter. In another example, the solid stress sensor 12 can include between one and eight pressure sensors 44 positioned around its outer perimeter. In the example shown in FIGS. 6A and 6B, the solid stress sensor 12 includes eight ultra-sensitive pressure sensors 46 (that is, 0 to 0.05 pounds per square inch, PSI, piezo-resistive gauges) stamped on thin, flexible bridges 48 (such as 0.02 mm nitinol foil created by micromachining). More specifically, two miniature strain gauges (0.2 by 0.8 millimeters) are stamped on each of the four bridges 48. In this example, each of the bridges 48 is coupled to the sensor tip 44 with flexible isolation to allow for deformation of the sensors 46. In the example shown in FIGS. 7A and 7B, four pressure sensors 46 are coupled between an outer perimeter structure 47 and a flexible, silicon central boss structure 49 of the sensor tip 44. In the example shown in FIGS. 8A and 8B, a plurality of pressure sensors 46 are stamped on a thin nitinol ultra-flexible tube 48. In this configuration, the nitinol tube 48 may be laser-welded or otherwise attached to sensor tip 44 that can act as a guiding wire. As illustrated in FIGS. 9A and 9B, the configuration may also include a flexible metallic coil 54 forming a tube. The flexible metallic coil 54 provides flexibility to rotational movements of the sensor tip and body during normal operation of an ultrasound endoscope.

Figure 6A:
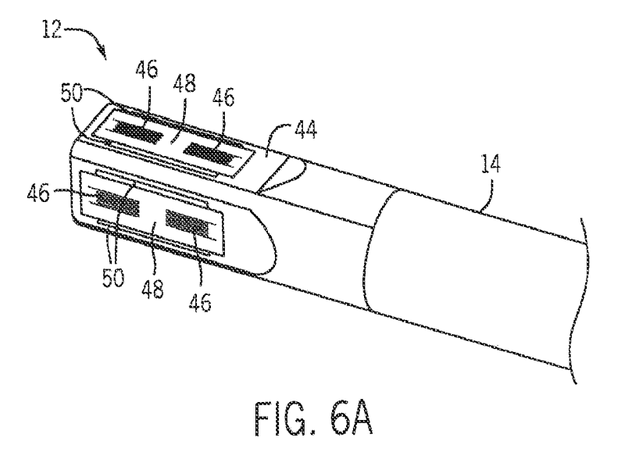
FIGS. 6A and 6B are perspective and cross-sectional views, respectively, of a solid stress sensor according to one implementation of the present disclosure.
Figure 6B:
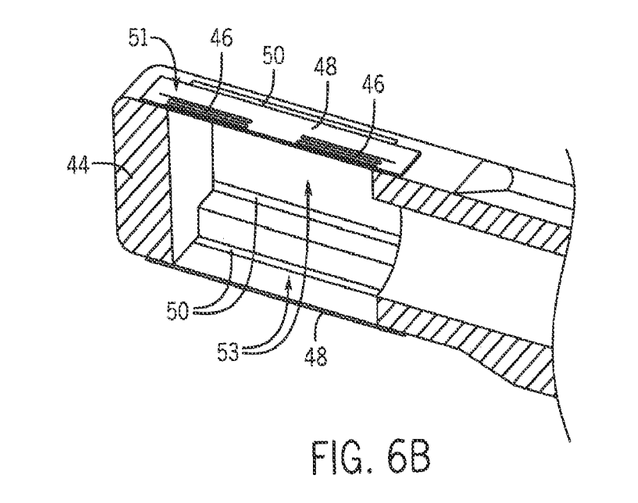
Figure 7A:
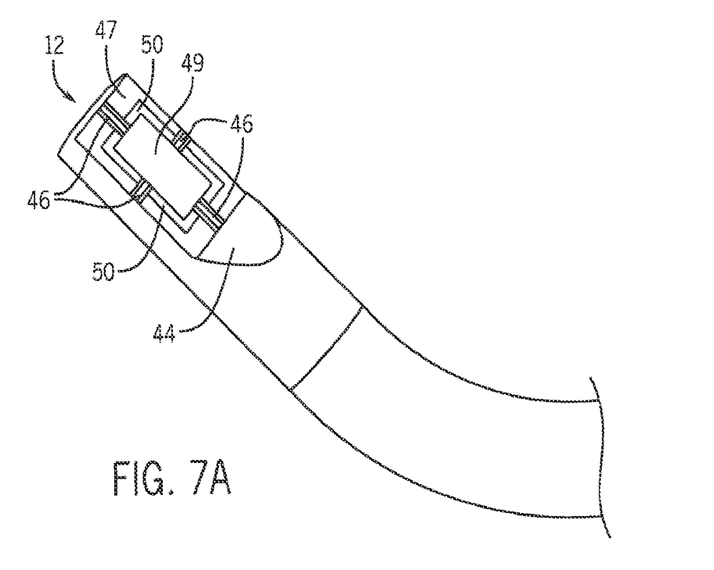
FIGS. 7A and 7B are perspective and cross-sectional views, respectively, of a solid stress sensor according to one implementation of the present disclosure.
Figure 7B:
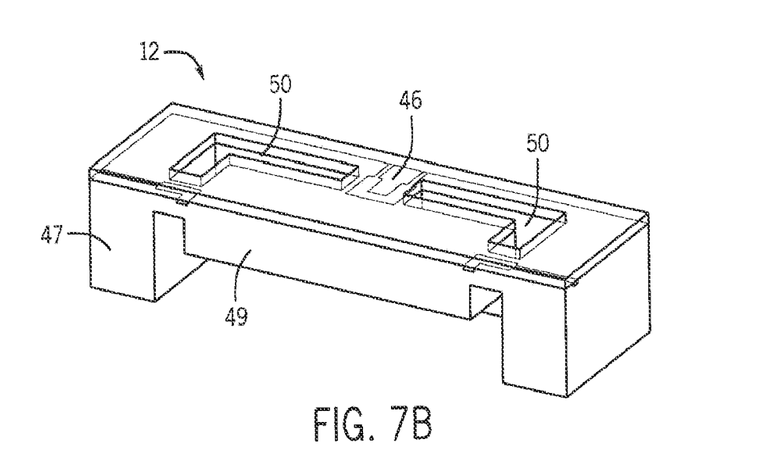
Figure 8A:
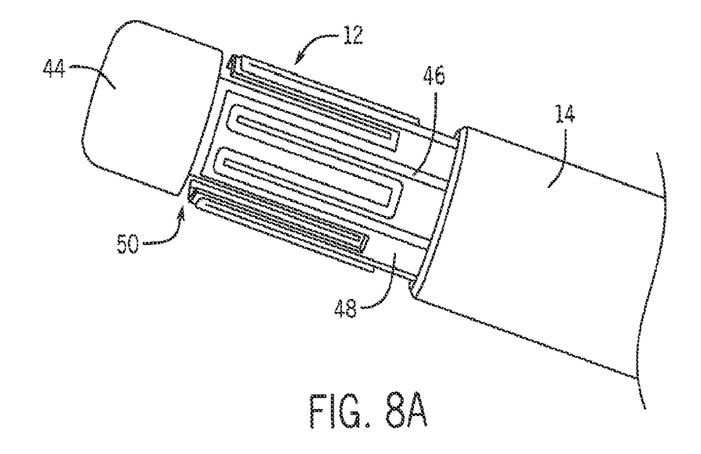
FIGS. 8A and 8B are perspective views of a solid stress sensor according to yet another implementation of the present disclosure and the solid stress sensor extending outward from a needle tip of a biopsy needle, respectively.
Figure 8B:
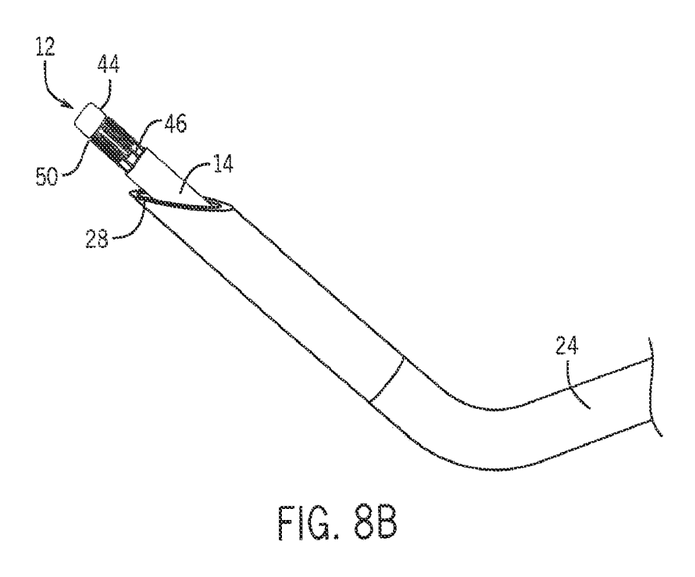
Figure 9A:
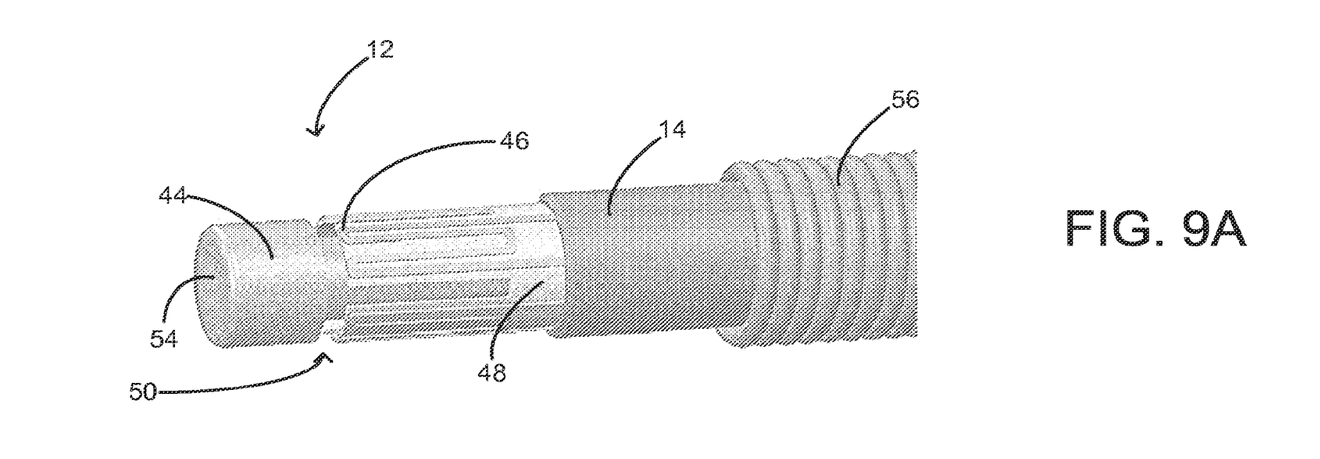
FIGS. 9A and 9B are a perspective view and a cross-sectional view, respectively, of a solid stress sensor according to yet another implementation of the present disclosure.
Figure 9B:
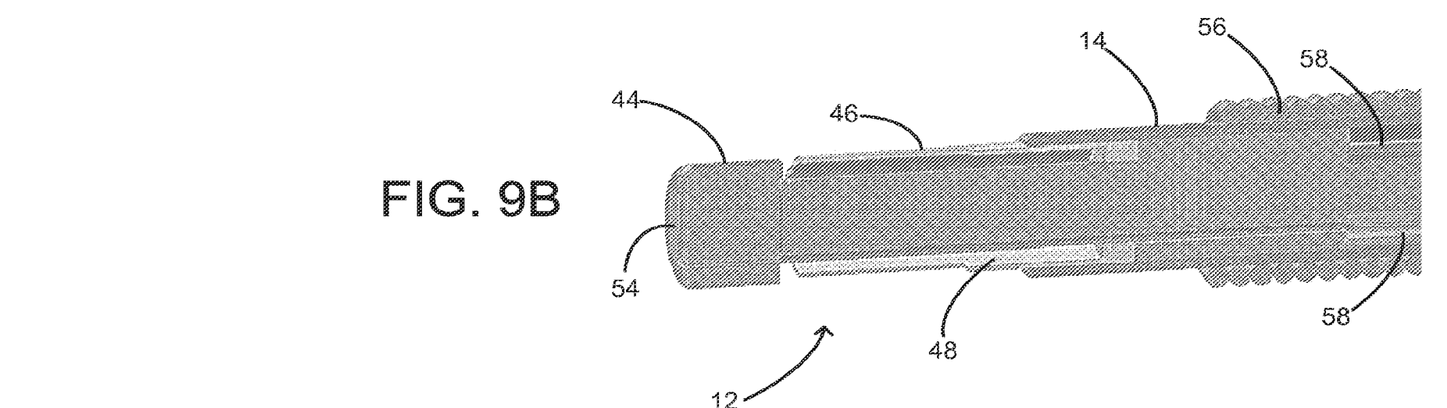

In light of the examples shown in FIGS. 6A-8B, the sensor tip 44 can include a square cross-sectional profile (as shown in FIGS. 6A-6B), a round cross-sectional profile (as shown in FIGS. 8A-8B), or an asymmetric cross-sectional profile (as shown in FIGS. 7A-7B). In addition, some pressure sensors may not require a flexible coupling with the sensor tip 44. In other words, the solid stress sensor 12 can include one or more rigid sensors 46 that do not need to deform in order to measure stresses. Furthermore, the sensor tip 44 can include a substantially blunt distal end (as shown in FIGS. 6A-8B) or a sharp distal end, and/or can include substantially flat perimeter surfaces (as shown in FIGS. 6A-7B) or protruding or round perimeter surfaces (as shown in FIGS. 8A-8B) for sensor mounting. As illustrated in FIGS. 9A and 9B, the sensor tip 44 may further include a piezo-resistive layer or coating 56 that may be configured to act as a contact sensor. The contact sensor can be used to measure the compressive stress applied to a tumor or soft tissue by compressing such a tumor or soft tissue from the outside with the contact sensor without penetrating such a tumor or soft tissue. The contact sensor can also be used inside the tumor, to measure the compressive stress while pressing against the tumor cells and stroma tissue (the other non-cancer cells and biological components) to measure the compliance of such cells and tissue separately from the interstitial fluid pressure. As shown in the cross-sectional view in FIG. 9B, electric wires 58 may be arranged to extend through an interior.

In accordance with implementations of the present disclosure, the solid stress sensor 12 can be configured to measure the stress on each piezo-resistor 46 from the tumor tissue, but not from fluid pressure. More specifically, the solid stress sensor 12 can be configured so that the interstitial fluid pressure will equalize on either, side of each pressure sensor 46, which is open to fluid but not solid tissue. For example, as shown in FIGS. 6A-8B, the sensor tip 44 can include one or more openings 50 to allow for fluid access to both sides of each pressure sensor 46. In other words, as best shown in FIG. 6B, an external side 51 facing outward from the sensor tip 44 and an opposite internal side 53 of each pressure sensor 46 are both accessible to fluid.

Furthermore, the pressure sensors 46 can be sized and configured to specifically measure solid stress. As a result, the pressure sensors 46 may be more robust than existing pressure sensors for interstitial fluid pressure measuring devices. The flexible metal spring tubing 14 can also be designed for robustness to effectively support the solid stress sensor 12. In addition, in some applications, the pressure sensors 46 can each have a sensing range from about 0 millimeters mercury (mmHg) to about 25.86 mmHg (as recent studies have shown that expected pressure values may range from about 0 mmHg to about 20 mmHg). Some applications of the present disclosure may also contemplate larger and/or higher ranges.

In light of the above-described solid stress sensor configuration with respect to operation of the device 10, when the biopsy needle 24 is extracted and the solid stress sensor 12 is exposed within the cylindrical opening 42, fluid pressure is equalized around each of the pressure sensors 46. However, the tissue surrounding the cylindrical opening 42 will start to relax against the pressure sensors 46, thus deforming each pressure sensor 46 and enabling measurement of solid stresses in that region. The mechanical signals caused by the mechanical deformations of each pressure sensor 46 can be converted into one or more electrical signals to be recorded and analyzed. More specifically, the sensor tip 44 can be coupled to the tubing 14 and electrical connectors (not shown) from each pressure sensor 46 can be routed through the tubing 14 to the data connector 20. The data acquisition system 22, coupled via the data connector 20, can receive the electrical signals for data processing and analysis and can output solid stress measurements to a user (such as in mmHg). For example, solid stress measurements can be output to the user via a display screen 52 of the data acquisition system 22, as shown in FIG. 2.

In applications that include a plurality of pressure sensors 46 positioned around the perimeter of the sensor tip 44, multiple solid stress measurements can be obtained, recorded, and analyzed relative to respective regions around the perimeter of the sensor tip 44. Accordingly, average, relative, or individual solid stress measurements can be output to the user. In some applications, the differences in individual solid stress measurements can provide additional information regarding properties of the tumor, such as non-uniformity of the tumor 40. In addition, in some applications, the solid stress sensor 12 can include one or more pressure sensors 46 to measure solid stress and one or more pressure sensors 46 to measure interstitial fluid pressure. More specifically, one or more pressures sensors 46 on the sensor tip 44 can be substantially sealed (that is, without openings 50 to allow fluid pressure to equalize on either side 51, 53 of the respective pressure sensor 46). In such applications, the system 10 can obtain and output both solid and fluid pressure measurements.

Accordingly, the present disclosure provides an in vivo and minimally invasive system and method to measure solid stress in a human soft tissue, an electro-mechanical microsensor for measuring tissue residual stress, and a catheter-based system to guide the microsensor into the tumor tissue. The system and method can be used to evaluate how compliant or rigid a tumor or soft tissue is from the exterior of the tumor of soft tissue without penetration, as well as being used to evaluate the interior biomechanical environment, for example, for fluid and solid stress pressures. Previously, devices have been developed for measuring interstitial fluid pressure in tumors and in soft tissues (such compartment syndrome in trauma). The present system can complement this previous technology by measuring forces transmitted by solid structural elements of the tissue rather than fluid pressures. This is accomplished using the electro-mechanical pressure microsensor to measure the solid stress separately from the hydrostatic fluid pressure. Furthermore, as described above, tumor biopsies are routinely collected via a catheter-based biopsy needle or forceps attached to an ultrasound endoscope at different stages during treatment to diagnose and stage the disease. Because the present system incorporates a catheter-based technology that can be used during a standard biopsy collection procedure, the present device can accurately measure the solid stress of a tumor at the same site where the biopsy is collected without disrupting the currently established diagnostic and treatment protocols, also providing the possibility to correlate the pathology results with device measurements. Solid stress monitoring, along with alleviating tumor solid stress, may significantly increase the efficiency of cancer treatment. Thus, implementations of the present disclosure can allow a superior staging of treatment, which can result in superior outcomes for the patient and substantial savings for the health system.

The present invention has been described in terms of one or more preferred embodiments, and it should be appreciated that many equivalents, alternatives, variations, and modifications, aside from those expressly stated, are possible and within the scope of the invention.

The invention claimed is:

1. A device for measuring solid stress in a tissue, the device comprising:
a tubing member with a distal end and a proximal end;
a sensor tip extending from the distal end of the tubing member to a tip end, wherein the sensor tip includes at least one opening extending along a portion of the sensor tip;
connection elements coupled to the proximal end of the tubing member; and
a sensor arranged within to the sensor tip and positioned on a flexible bridge, the flexible bridge extending over the at least one opening and extending beyond a boundary defined by the at least one opening, the flexible bridge being coupled to the sensor tip, wherein a gap is arranged between the flexible bridge and an edge of the at least one opening, wherein the sensor includes an internal-facing side and an external-facing side, wherein the gap between the flexible bridge and the edge of the at least one opening is configured to allow fluid access to the internal-facing side and the external-facing side, wherein the fluid access to the internal-facing side and the external-facing side is configured to enable the sensor to measure solid stress independently of fluid pressure.

2. The device of claim 1, wherein the connection elements include a biopsy needle mount and a data connector.

3. The device of claim 2, wherein the data connector is configured to connect to one of a data acquisition system, a personal computer, and a data processing system.

4. The device of claim 1, wherein the tubing member and the sensor tip are sized to enable routing of the tubing and the sensor tip through a biopsy needle.

5. The device of claim 1, wherein the flexible bridge includes two piezo-resistor component stamped onto the flexible bridge at locations that are separated from one another.

6. The device of claim 1, wherein the sensor includes eight piezo-resistor components, wherein corresponding pairs of the eight piezo-resistor components are arranged on different sides of the sensor tip.

7. The device of claim 1, wherein the sensor includes four piezo-resistor components, each of the four piezo-resistor components being arranged on a different side of the sensor tip.

8. The device of claim 1, wherein the sensor is coupled around an outer perimeter of the sensor tip.

9. The device of claim 1, wherein the sensor tip includes one of a square, round, and asymmetric cross-sectional profile.

10. The device of claim 1, wherein the tubing member is flexible metal tubing.

11. The device of claim 1, wherein the sensor tip includes a piezo-resistor contact sensor.

12. The device of claim 1, wherein a first end of the flexible bridge is coupled to the sensor tip at a first location on the sensor tip, a second end of the flexible bridge is coupled to the sensor tip at a second location on the sensor tip, the first location and the second location being arranged outwardly from the boundary defined by the at least one opening.

* * * * *

UNITED STATES PATENT AND TRADEMARK OFFICE
CERTIFICATE OF CORRECTION

| | |
|---|---|
| PATENT NO. | : 11,259,714 B2 |
| APPLICATION NO. | : 14/892380 |
| DATED | : March 1, 2022 |
| INVENTOR(S) | : Gabriel Gruionu et al. |

It is certified that error appears in the above-identified patent and that said Letters Patent is hereby corrected as shown below:

In the Specification

Column 8, Claim 1, Line 11, "arranged within to" should be --arranged adjacent to--.

Signed and Sealed this
Seventeenth Day of May, 2022

*Katherine Kelly Vidal*

Katherine Kelly Vidal
*Director of the United States Patent and Trademark Office*